United States Patent [19]

Rahman

[11] Patent Number: 4,952,408

[45] Date of Patent: Aug. 28, 1990

[54] LIPOSOME-ENCAPSULATED VINCA ALKALOIDS AND THEIR USE IN COMBATTING TUMORS

[75] Inventor: Aquilur Rahman, Gaithersburg, Md.

[73] Assignee: Georgetown University, Washington, D.C.

[21] Appl. No.: 197,648

[22] Filed: May 23, 1988

[51] Int. Cl.$^5$ .................. A16K 37/22; B01J 13/02
[52] U.S. Cl. .................. 424/450; 428/402.2; 514/883; 514/908
[58] Field of Search .......... 424/450; 264/4.6; 428/402.2; 436/829; 514/883, 908

[56] References Cited

U.S. PATENT DOCUMENTS

| | | | |
|---|---|---|---|
| 4,331,654 | 5/1982 | Morris | 424/450 |
| 4,362,664 | 12/1982 | Gerzon et al. | 514/908 X |
| 4,479,957 | 10/1984 | Cullinan et al. | 514/883 X |
| 4,565,696 | 1/1986 | Heath et al. | 424/450 |
| 4,663,167 | 5/1987 | Lopez-Berenstein et al. | 514/37 |
| 4,711,782 | 12/1987 | Okada et al. | 264/4.6 X |

FOREIGN PATENT DOCUMENTS

WO86/01102  2/1986  PCT Int'l Appl. ............ 424/450

OTHER PUBLICATIONS

*The Merck Index*, 10th edition, Merck and Co., Inc., Rahway, N.J., U.S.A., 1983, pp. 1427–1429.

Primary Examiner—Matthew A. Thexton
Assistant Examiner—Daniel S. Metzmaier
Attorney, Agent, or Firm—Oblon, Spivak, McClelland, Maier & Neustadt

[57] ABSTRACT

A composition made up of a liposome-encapsulated vinca alkaloid is disclosed. This composition possesses an increased antitumor activity and a substantially lower toxicity as compared to free drug.

11 Claims, 5 Drawing Sheets

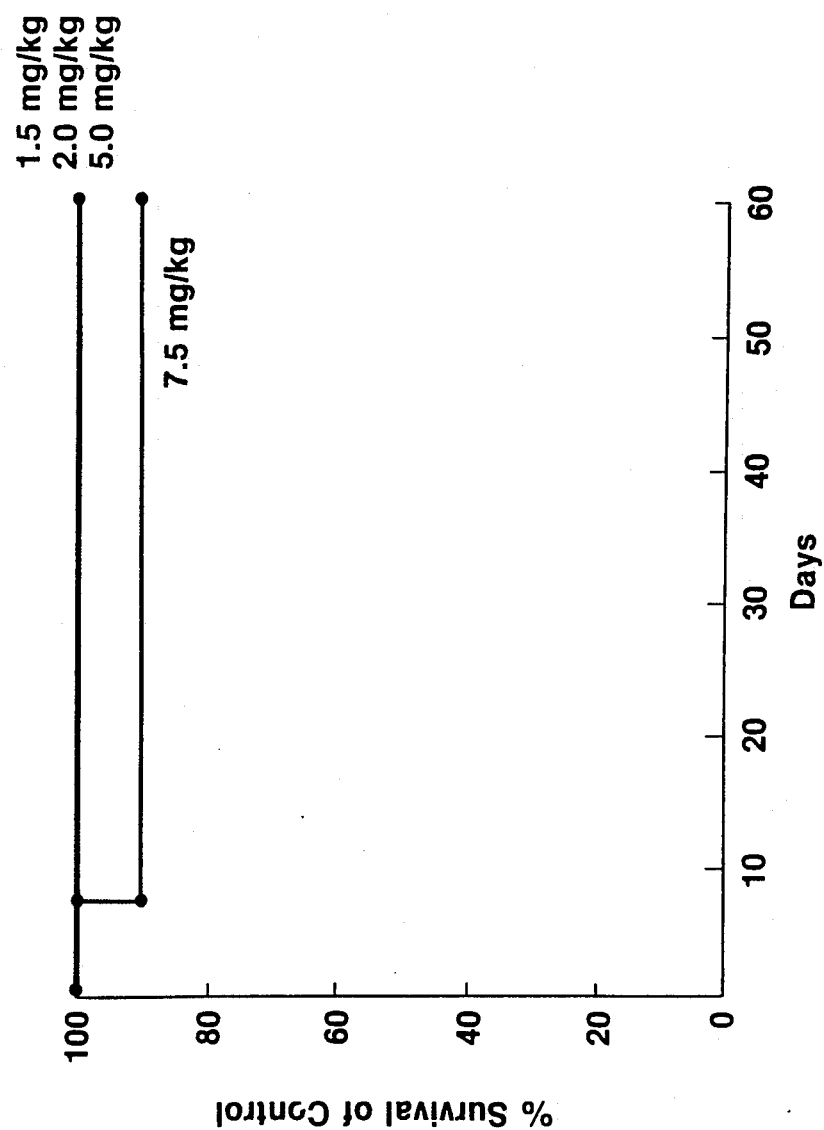

LIPOSOME-ENCAPSULATED VINCA ALKALOIDS AND THEIR USE IN COMBATTING TUMORS

BACKGROUND OF THE INVENTION

1. Field of the Invention

The present invention relates to the use of vinca alkaloids in combatting tumors.

2. Discussion of the Background

The dimeric alkaloids, vincristine and vinblastine, containing indol-indoline moieties from Catharanthus species are widely used as antitumor agents, singly or in combination with other chemotherapeutic agents. Vincristine has demonstrated substantial activity against non-Hodgkin's and Hodgkins lymphomas, acute lymphoblastic leukemia, Wilm's tumor, rhabdomyosarcoma, and neuroblastoma.

The vinca alkaloids possess cytotoxic activity by virtue of their binding to tubulin. The latter is a dimeric protein found in the soluble fraction of the cytoplasm of all cells. It exists in equilibrium with a polymerized form, the microtubular apparatus which forms the spindle along which chromosomes migrate during mitosis. In addition, microtubules play a vital role in maintaining cell structure, providing a conduit for cellular secretions and for neurotransmitters transit along axons. The vinca alkaloids, through their binding to tubulin, inhibit the process of assembly of microtubules and lead to the dissolution of the mitotic spindle.

The clinical use of vincristine is highly compromised because of treatment-limiting toxicities. Total doses of vincristine in excess of 2 mg are often associated with a progressive and disabling neurotoxicity. The first signs of neuropathy are a decrease in deep tendon reflexes and paresthesias of the fingers and lower extremeties. More advanced neurotoxicity may lead to cranial nerve palsies and profound weakness of the dorsiflexors of the foot and extensors of the wrist. At higher doses of vincristine, above 3 mg total dose, constipation, obstipation and paralytic ileus may occur because of autonomic neuropathy.

The vincristine alkaloid, like many other antineoplastic drugs, fails to discriminate efficiently between normal and target tissues. A system enabling such chemotherapeutic agents to reach their target in a selective and controlled fashion would represent a substantial advance in cancer chemotherapy.

SUMMARY OF THE INVENTION

Accordingly, it is an object of this invention to provide a chemotherapeutic composition which does not suffer the above-noted disadvantages.

It is another object of this invention to provide a chemotherapeutic composition which enables the chemotherapeutic agent to reach its target in a selective fashion.

It is another object of this invention to provide a chemotherapeutic composition which enables the chemotherapeutic agent to reach its target in a controlled fashion.

It is another object of this invention to provide a chemotherapeutic composition having an enhanced antitumor effect.

It is another object of this invention to provide a chemotherapeutic composition having decreased toxicity.

The inventor has discovered a composition which satisfies all of these objects of this invention and other objects which will become apparent from the description of the invention given hereinbelow. This composition is a composition which contains at least one liposome encapsulated vinca alkaloid. The vinca alkaloid is vincristine, vinblastine, vindesine, or a combination of these.

BRIEF DESCRIPTION OF THE FIGURES

A more complete appreciation of this invention and many of its attendant advantages will be readily obtained as the same becomes better understood by reference to the following detailed description when considered in connection with the accompanying figures.

FIG. 5 illustrates the toxicity of liposomal vincristine in mice.

DETAILED DESCRIPTION OF THE PREFERRED EMBODIMENTS

Figure 1:
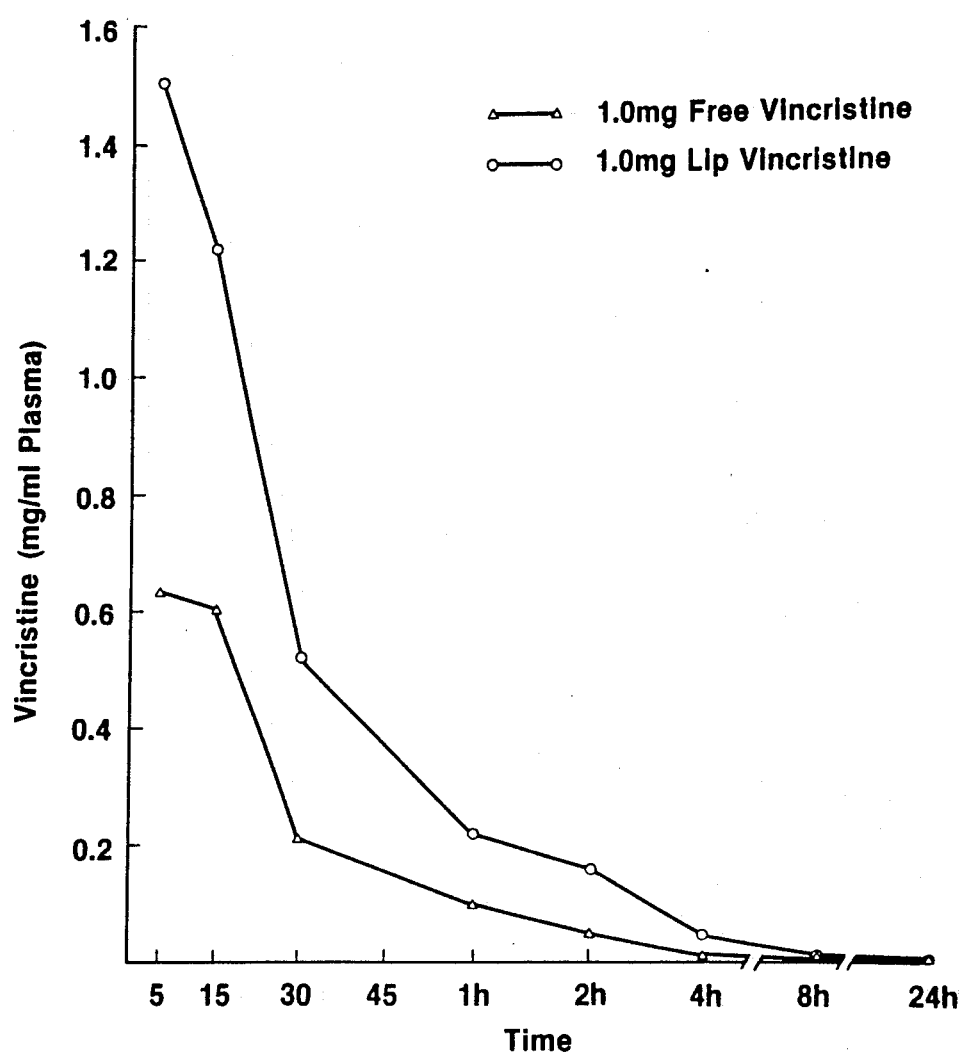
FIG. 1 illustrates the plasma pharmacokinetics of free and liposomal vincristine.

The inventor has now discovered a novel method of encapsulating vincristine, vinblastine, vindesine (deacetyl vinblastine), or a combination of these in liposomes. This discovery has made possible the further discovery that the pharmacokinetic and tissue distribution of liposomal vinca alkaloids is substantially altered with a pronounced increase in antitumor activity and a substantial reduction in toxicities as compared to the free drug.

The liposomal encapsulated vinca alkaloid composition of the present invention represents a novel approach in cancer therapy. The dose limiting toxicities of free chemotherapeutic agent are effectively alleviated by liposomal encapsulation hence higher doses can be administered. In addition, equivalent doses of drug entrapped in liposomes provide much higher therapeutic responses which is not yet seen with any anticancer agent with any modality of treatment based on carrier system. Though the mechanism is not fully understood, in part, it appears to altered pharmacokinetics of the drug when it is administered entrapped in liposomes.

Thus the present invention provides a composition comprising liposome-encapsulated vinca alkaloid(s). the liposome-encapsulated vinca alkaloid(s) can be liposome encapsulated vincristine, liposome-encapsulated vinblastine, liposome-encapsulated vindesine, or a liposome encapsulated combination of at least two of vincristine, vinblastine, and vindesine.

The liposome-encapsulated material can be obtained by dissolving either the vinca alkaloid free base or a salt thereof (e.g. the sulfate or ammonium salt) in a solvent. When the free base form of the vinca alkaloid is used, the solvent is preferably a relatively nonpolar organic solvent. When the salt form is used the solvent used is preferably a polar organic solvent, e.g., methanol or ethanol. When the vinca alkaloid is completely dissolved in the solvent, the dissolved vinca alkaloid is complexed with cardiolipin by adding a solution of cardiolipin to the solvated chemotherapeutic agent.

The solvent used to dissolve the cardiolipin can be methanol or ethanol.

The mixture obtained is then stirred gently and evaporated under an inert atmosphere to dryness. The inert atmosphere can be nitrogen, argon, or a combination of these two.

To this dried mixture, one then adds phosphatidylcholine, cholesterol and either phosphatidylserine or dicetylphosphate (DCP). The mixture obtained is then stirred gently to achieve a homogeneous solution and evaporated to dryness under an inert atmosphere to produce lipids and drug films.

The dried lipids are then resuspended in a solution where they are hydrated and then sonicated. The solution used can be a saline solution, a phosphate buffered saline, a lactose solution, a glucose solution, a mannitol solution, or any other known physiologic buffered solution. Non-entrapped vinca alkaloid is separated from the liposome-encapsulated vinca alkaloid by dialysis and/or high speed centrifugation.

If desired, the liposome encapsulated vinca alkaloid can then be lypholized to permit storage. If the liposome-encapsulated vinca alkaloid is stable in solution however, it can be stored in a saline or lactose medium.

In the above preparation, the relative amounts of the components used to prepare the liposome-encapsulated vinca alkaloid are as follows. The vinca alkaloid is used in an amount of from 6.8 parts by weight to 9.2 parts by weight. The cardiolipin is used in an amount of from 30.6 parts by weight to 41.4 parts by weight. The phosphtidylcholine is used in an amount of from 102 parts by weight to 138 parts by weight. The cholesterol is used in an amount of from 34 parts by weight to 46 parts by weight. And the phosphatidylserine or dicetylphosphate is used in an amount of from 6.8 parts by weight to 9.2 parts by weight.

These liposome-encapsulated chemotherapeutic compositions are useful in the treatment of non-Hodgkin's and Hodgkin's lymphomas, acute lymphoblastic leukemia, Wilm's tumor, rhabdomyosarcoma, and neuroblastoma. In the treatment of these tumors, the liposome-encapsulated chemotherapeutic agent dissolved in an appropriate pharmaceutical carrier or excipient is administered intravenously either as a bolus or continuously over a period of from 5 minutes to 30 minutes. In continuous administration, the liposome-encapsulated therapeutic agent suspended in an appropriate pharmaceutical carrier or excipient can be delivered by osmotic pump.

Carriers which can be used in the present invention include suitable pharmaceutically acceptable carriers comprising excipients and auxiliaries which facilitate processing of the active compounds into preparations which can be used pharmaceutically. Suitable formulations for intravenous administration of the active compound may include suspensions of the active ingredients.

Solutions for administrations intravenously contain from about 0.1 to about 99.5% by weight, and preferably from about 25 to 85% by weight, of active ingredient, together with the excipient.

The dose and the route of administration and the carrier and/or adjuvants used may vary based on the tumor type being treated and in view of known procedures for treatment of such tumors. Typically the dose of administration is from 1.2 to 1.6 mg. of vinca alkaloid per $m^2$ in humans.

Other features of this invention will become apparent in the course of the following descriptions of exemplary embodiments which are given for illustration of the invention and are not intended to be limiting thereof.

LIPOSOMAL ENCAPSULATION

To encapsulate vincristine in liposomes, various lipid constituents were investigated and percent efficiency of the drug entrapped in liposomes was determined. The best combination of lipids which is developed in our laboratories is as follows:

Vincristine sulfate, 8 mg, was dissolved in methanol and stirred gently to achieve a clear solution, and was complexed with 36 mg of cardiolipin in ethanol. The mixture was stirred gently and evaporated under $N_2$ to dryness. To this dried mixture were then added 120 mg of phosphatidylcholine, 40 mg of cholesterol and 8 mg of phosphatidylserine. The mixture was stirred gently to achieve a homogeneous solution and evaporated to dryness under $N_2$. The dried lipids were resuspended in 0.9% NaCl solution, hydrated for ½ hr. in the dark and then sonicated in a cup-horn sonicator at 37° C. for 30 minutes. The non-entrapped vincristine was separated from liposomal encapsulated drug by extensive dialysis against 0.9% NaCl at 4° C. for 24 hours with at least 3 changes of saline solution. The percentage of entrapment of vincristine in liposomes was determined spectrophometrically after the completion of dialysis and was found to be 70% (N=7) of the total input dose.

Figure 2:
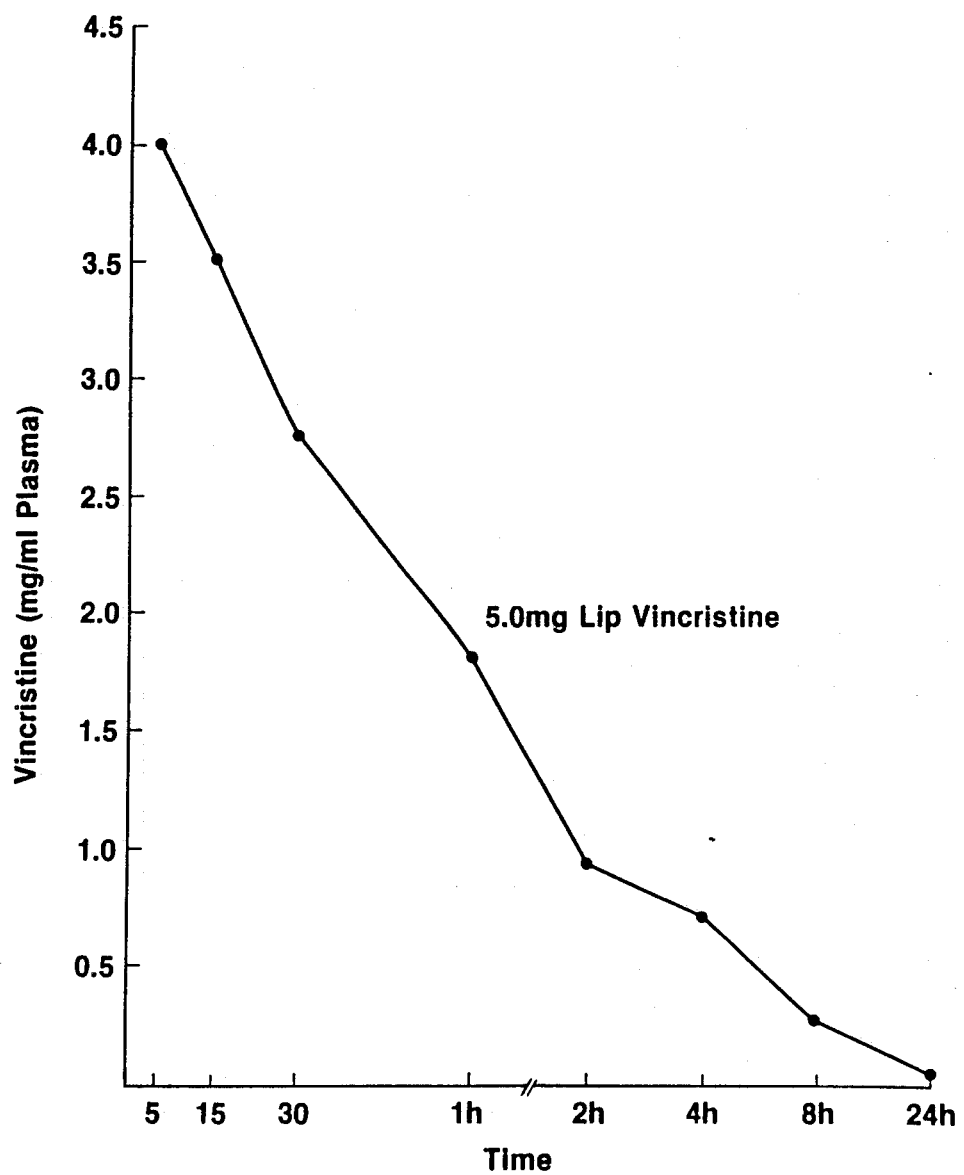
FIG. 2 illustrates the plasma pharmacokinetics of liposomal vincristine at a dose of 5 mg $kg^{-1}$ i.v.

PHARMACOLOGIC DISPOSITION STUDIES $CD_2F_1$ mice were administered vincristine as a free drug at a dose of 1 mg $kg^{-1}$ and liposomal entrapped vincristine at a dose of 1 mg $kg^{-1}$ and 5 mg $kg^{-1}$ via a lateral tail vein. At sequential time points, four mice in each treatment group were sacrificed and specific tissues were isolated and assayed for drug levels by radioimmunoassay as adapted in our laboratories. The plasma pharmacokinetics of free vincristine and liposomal vincristine is presented in FIGS. 1 and 2.

With a dose of 1 mg $kg^{-1}$ of free vincristine, the peak plasma level at 5 minutes is 0.62 $\mu g$ $ml^{-1}$ whereas the liposomal vincristine at doses of 1 mg $kg^{-1}$ and 5 mg $kg^{-1}$ provides a peak plasma level of 1.5 $\mu g$ $ml^{-1}$ and 4.0 $\mu g$ $ml^{-1}$ at 5 minutes respectively. From 5 minutes to 2 hours, the plasma levels with liposomal vincristine are at least four-fold higher than free vincristine at equivalent doses. The dose of 5 mg $kg^{-1}$ of liposomal vincristine provides a much higher plasma level from 5 minutes to 24 hours when compared to 1 mg $kg^{-1}$ dose of either free vincristine or liposomal vincristine.

The administration of free vincristine provide a much faster clearance of drug from plasma with an apparent large volume of distribution. However, with liposomal administration of vincristine, the clearance of drug from plasma is considerably delayed.

Table 1 presents the measurements of drug concentration in selected tissues following administration of free and liposomal entrapped vincristine. The drug levels in liver at 2 hours with free vincristine were 50 ng $gm^{-1}$ of tissue and were 125 and 260 ng $gm^{-1}$ of tissue with 1 and 5 mg $kg^{-1}$ dose of liposomal vincristine, respectively. However, the drug levels in liver by 8 hours were undetectable with free vincristine, whereas with liposomal vincristine they were 75 and 160 ng $gm^{-1}$ of tissue at doses of 1 and 5 mg $kg^{-1}$ respectively. In addition, the drug levels in spleen at all time periods of observation are 2 to 3 fold higher with liposomal vincristine compared to free vincristine. In contrast, the levels of drug in brain following administration of free vincristine were higher than liposomal vincristine at either 1 mg kg$^{-1}$ or 5 mg kg$^{-1}$ dose. The levels in lung, following administration of 1 mg kg$^{-1}$ dose of either free or liposomal vincristine were comparable at different periods of observation (Table 1).

IN VITRO CYTOTOXICITY EVALUATION AGAINST L1210 LEUKEMIA CELLS

Figure 3:
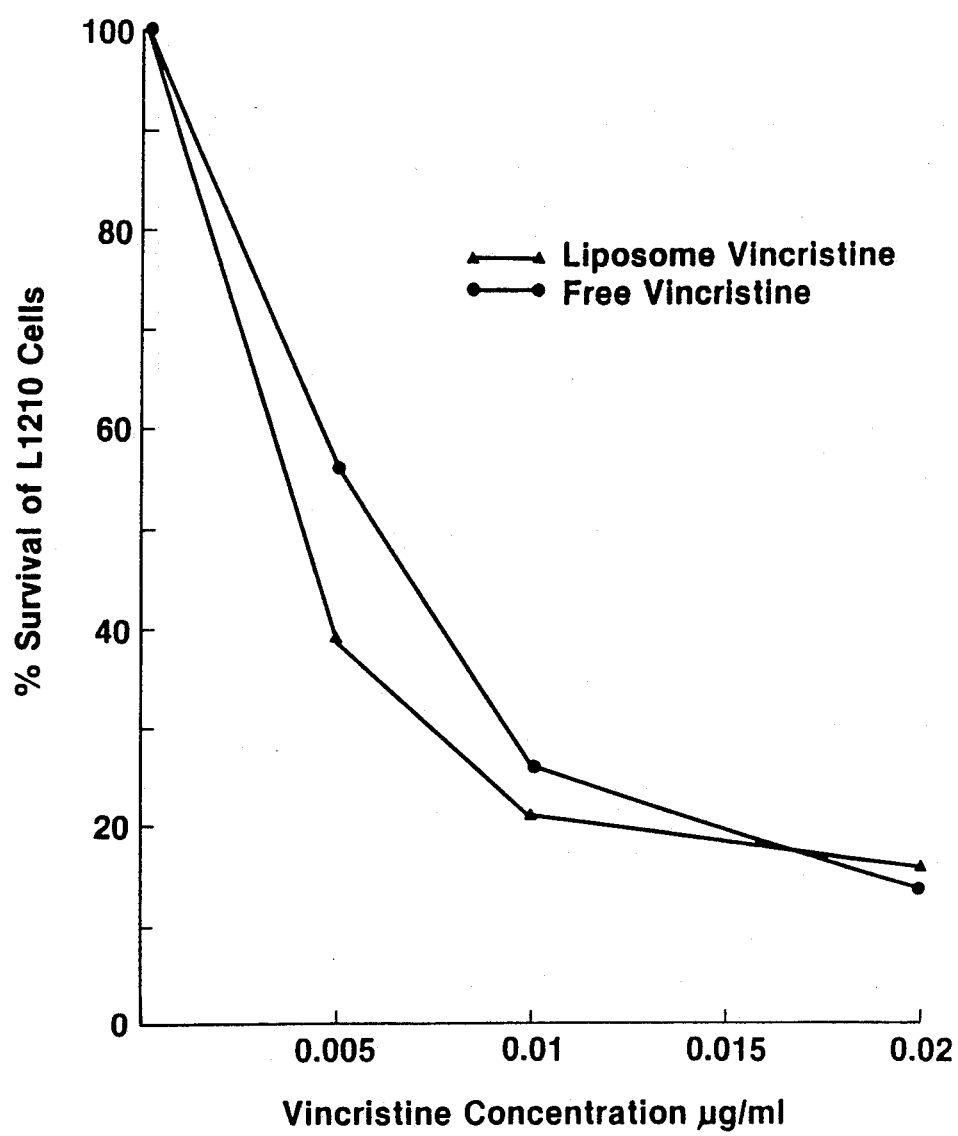
FIG. 3 illustrates the cytotoxicity of free and liposomal vincristine in L1210 leukemia after 72 hours of drug exposure.

L1210 Leukemia cells were grown in suspension in air with 5% $CO_2$ in RPMI Medium 1640 supplemented with 10% fetal calf serum and gentamicin (50 μg/ml). Log phase cells (10 ml) at an innoculum of $1 \times 10^5$ cells/ml of medium in 25 cm$^2$ plastic flasks were treated with either free vincristine or liposomal entrapped vincristine at different doses for 24 hours at 37° C. After drug treatment, cells were transferred to Falcon tubes and centrifuged for 10 minutes at 600 rpm. The supernatant media were discarded and the cell pellet was washed 3 times with RPMI Media 1640. The final cell pellet was resuspended in 10 ml of RPMI media and transferred to 25 cm$^2$ plastic flasks and incubated at 37° C. in air with 5% $CO_2$ for growth. At 48 and 72 hours, an aliquot of cells from each flask were taken and were counted for viability by trypan blue exclusion under microscope. The number of cells proliferating in each flask were determined with respect to control. FIG. 3 represents the percent survival of cells when treated with free vincristine or vincristine entrapped in liposomes. As it appears, the IC$_{50}$ for L1210 murine leukemia cells with free vincristine is 0.004 μg/ml whereas the IC$_{50}$ for liposomal vincristine is 0.003 μg/ml. This experiment shows that vincristine encapsulated in liposomes possesses equivalent cytotoxicity in vitro against leukemia cells.

ANTITUMOR STUDIES WITH L1210 MURINE LEUKEMIA IN MICE

The L1210 leukemia was maintained by serial passage i.p. in DBA/2F$_1$ female mice. For antitumor studies, $2 \times 10^5$ cells of L1210 leukemia were implanted i.p. in CD$_2$F$_1$ male mice (22–25 g). Twenty-four hours after tumor implantation, the mice were injected intravenously with a single dose of 2 mg/kg and 3 mg/kg of free vincristine and 2, 3, 5.0 and 7.5 mg/kg single doses of liposomal vincristine. Each drug treated group and saline treated leukemic control group was composed of eight mice. Each animal was observed for day of death. Data are expressed as % of ILS (percentage of increase in life span). Median life spans were calculated from grouped median survival times and % of increase in life was calculated as:

$$100 \times \frac{\text{Median survival time of treated mice}}{\text{Median survival time of control mice}} - 100$$

Experiments were terminated on day 50. Mice alive on that day were termed "cures" and were included in the calculation of median survival time of treated mice. The results were presented in Table 2. The saline treated or blank liposomes treated controls had the median survival of 11 days. Free vincristine at a dose of 2 mg kg$^{-1}$ provided a median survival of 14.5 days with a % ILS of 32 with 2/8 long-term survivals. The dose of 3 mg kg$^{-1}$ of free vincristine produced a median survival of these tumor bearing mice of 7.5 days with an ILS of −32% exhibiting that the tumor bearing mice died of drug toxicity rather than tumor. All the animals in this group were dead by day 10. In contrast, the doses of vincristine entrapped in liposomes provided a much higher therapeutic response in mice bearing L1210 leukemia. For example, the dose of 2 mg kg$^{-1}$ of liposomal vincristine produced an ILS of >22354% with 4/8 of mice surviving on day 50. In addition, higher doses of vincristine administered in liposomes produced significant therapeutic response with majority of leukemia bearing mice surviving at day 50. The dose of 3.0, 5.0 and 7.5 mg kg$^{-1}$ of liposomal vincristine produced >354% ILS with 6/8, 7/8 and 4/8 long term survivors respectively (Table 2).

TOXICITY EVALUATION OF FREE VINCRISTINE AND LIPOSOMAL VINCRISTINE IN NORMAL MICE

Figure 4:
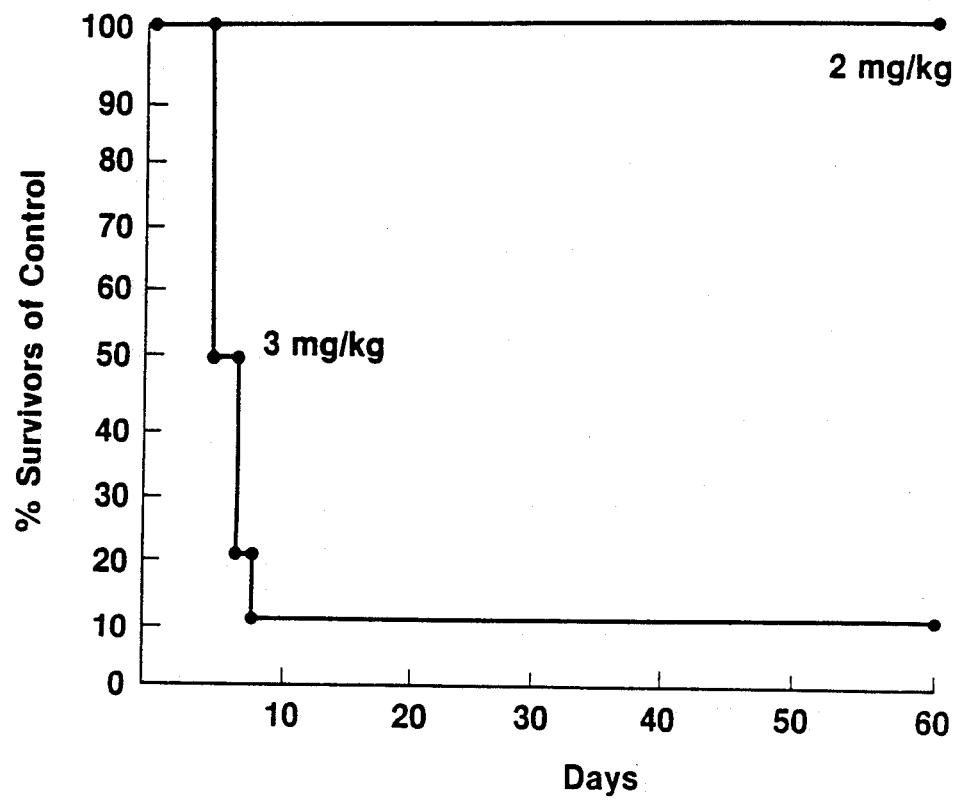
FIG. 4 illustrates the toxicity of free vincristine in mice.

The studies performed in mice bearing L1210 leukemia showed that the tolerance of liposomal vincristine is enhanced with a concurrent increase in therapeutic activity. Hence, lethal toxicity of free vincristine and vincristine entrapped in liposomes was evaluated in mice as a function of the dose of the drug. Normal CD$_2$F$_1$ mice were administered single injections i.v. of free vincristine at doses of 2 mg kg$^{-1}$ and 3 mg kg$^{-1}$ and liposomal vincristine was administered as single doses of 1.5, 2.0, 5.0 and 7.5 mg kg$^{-1}$ i.v. The mice were observed daily for death and weighed twice weekly to record changes in body weight due to toxicity. As shown in FIG. 4 and 5 mice injected with free vincristine at a dose of 2 mg kg$^{-1}$ survived until day 60, the day when experiment was terminated, without any lethality. However, mice which received doses of 3 mg kg$^{-1}$ of free vincristine exhibited pronounced lethality and 90% of the mice were dead by day 8. In contrast, mice which received doses of 1.5, 2.0, and 5.0 mg kg$^{-1}$ of liposomal vincristine did not show any lethality and 100% survival was achieved on day 60. With liposomal vincristine at a dose of 7.5 mg kg$^{-1}$, only one animal died on day 7 and rest of the animals in the group survived until day 60. This experiment demonstrates that higher doses of vincristine in liposomes can be administered to mice without any toxicity.

TABLE 1

| Drug | VINCRISTINE LEVELS | | | | | | | |
|---|---|---|---|---|---|---|---|---|
| | 5' | 15' | 30' | 1h | 2h | 4h | 8h | 24h |
| LUNG ng/gm Tissue | | | | | | | | |
| 1.0 mg Free | 80.0 | 78.0 | 80.0 | 75.0 | 77.0 | 64.0 | 58.0 | 4.0 |
| 1.0 mg Lip. | 78.0 | 78.0 | 78.0 | 50.0 | 65.0 | 75.0 | 45.0 | 4.0 |
| 5.0 mg Lip. | 140.0 | 140.0 | 110.0 | 110.0 | 120.0 | 85.0 | 78.0 | 64.0 |
| KIDNEY ng/gm Tissue | | | | | | | | |
| 1.0 mg Free | 65.0 | 64.0 | 62.0 | 47.0 | 47.0 | 20.0 | 18.0 | 2.0 |
| 1.0 mg Lip. | 65.0 | 62.0 | 62.0 | 55.0 | 47.0 | 40.0 | 30.0 | 4.0 |
| 5.0 mg Lip. | 104.0 | 104.0 | 100.0 | 64.0 | 64.0 | 47.0 | 21.0 | 21.0 |
| LIVER ng/gm Tissue | | | | | | | | |
| 1.0 mg Free | 200 | 161 | 121 | 84 | 47 | 10 | — | — |
| 1.0 mg Lip | 200 | 151 | 151 | 115 | 114 | 85 | 72 | 12 |
| 5.0 mg Lip. | 425 | 381 | 344 | 322 | 260 | 185 | 160 | 72 |
| SPLEEN ng/gm Tissue | | | | | | | | |
| 1.0 mg Free | 83 | 84 | 72 | 86 | 112 | 112 | 61 | 43 |
| 1.0 mg Lip. | 168 | 201 | 200 | 180 | 180 | 180 | 120 | 92 |
| 5.0 mg Lip. | 120 | 216 | 186 | 186 | 188 | 183 | 225 | 182 |
| BRAIN ng/gm Tissue | | | | | | | | |
| 1.0 mg Free | 28.0 | 21.0 | 20.0 | 21.0 | 21.0 | 29.0 | 29.0 | 19.0 |
| 1.0 mg Lip. | 11.6 | 11.6 | 19.0 | 19.0 | 11.0 | 11.0 | 7.0 | 6.0 |
| 5.0 mg Lip. | 11.6 | 11.0 | 2.5 | 2.5 | 2.5 | 4.8 | 2.0 | 0.5 |

TABLE 1-continued

| Drug | VINCRISTINE LEVELS | | | | | | | |
|---|---|---|---|---|---|---|---|---|
| | 5' | 15' | 30' | 1h | 2h | 4h | 8h | 24h |
| | PLASMA LEVELS ug/ml | | | | | | | |
| 1.0 mg Free | 0.63 | 0.6 | 0.2 | 0.1 | 0.05 | — | — | — |
| 1.0 mg Lip. | 1.52 | 1.24 | 0.54 | 0.23 | 0.16 | 0.05 | — | — |
| 5.0 mg Lip. | 4.0 | 3.5 | 2.75 | 1.6 | 0.9 | 0.69 | 0.26 | 0.05 |

TABLE 2

Antitumor Evaluation of Free Vincristine and
Liposomal Vincristine Against L1210 Leukemia in Mice

| Drug | Dose (mg/kg) | Median Survival (days) | % ILS | Long Term Survivors (50 days) |
|---|---|---|---|---|
| Saline | — | 11.0 | 0 | 0/8 |
| Blank Liposomes (Empty Liposomes) | — | 11.0 | 0 | 0/8 |
| Free Vincristine | 2.0 | 14.5 | 32 | 2/8 |
| — | 3.0 | 7.5 | −32 | 0/8 |
| Liposomal | 2.0 | >50.0 | >354 | 4/8 |
| — | 3.0 | >50.0 | >354 | 6/8 |
| — | 5.0 | >50.0 | >354 | 7/8 |
| — | 7.5 | >50.0 | >354 | 4/8 |

$CD_2F_1$ mice were implanted intraperitoneally with $2 \times 10^5$ leukemia cells and drug treatment was given intravenously on day 1 with varying doses of free and liposomal vincristine.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition, comprising a liposome-encapsulated effective amount of a vinca alkaloid in complexation with cardiolipin, said vinca alkaloid being at least one member selected from the group consisting of vincristine, vinblastine and vindesine.

2. The composition of claim 1, wherein said vinca alkaloid is vincristine.

3. The composition of claim 1, wherein said vinca alkaloid is vinblastine.

4. The composition of claim 1, wherein said vinca alkaloid is vindesine.

5. The composition of claim 1, which comprises from 6.8 to 9.2 parts by weight of vinca alkaloid, from 30.6 to 41.4 parts by weight of cardiolipin, from 102 to 138 parts by weight of phosphatidylcholine, from 34 to 46 parts by weight of cholesterol and from 6.8 to 9.2 parts by weight of phosphatidylserine or dicetylphosphate.

6. A method of treating a tumor in a patient in need thereof, comprising administering to said patient an effective amount of a pharmaceutical composition, comprising a liposome-encapsulated effective amount of a vinca alkaloid in complexation with cardiolipin, said vinca alkaloid being at least one member selected from the group consisting of vincristine, vinblastine and vindesine.

7. The method of claim 6, wherein said vinca alkaloid is vincristine.

8. The method of claim 6, wherein said vinca alkaloid is vinblastine.

9. The method of claim 6, wherein said vinca alkaloid is vindesine.

10. The method of claim 6, wherein said tumor is a tumor caused by a non-hodgkin's lymphoma, Hodgkin's lymphoma, acute lymphoblastic leukemia, Wilm's tumor, rhabdomyosarcoma and neuroblastoma.

11. The method of claim 6, wherein said pharmaceutical composition comprises from 6.8 to 9.2 parts by weight of vinca alkaloid, from 30.6 to 41.4 parts by weight of a cardiolipin, from 102 to 138 parts by weight of phosphatidylcholine, from 34 to 46 parts by weight of cholesterol and from 6.8 to 9.2 parts by weight of phosphatidylserine or dicetylphosphate.

* * * * *